United States Patent [19]

Hartlaub et al.

[11] Patent Number: 5,115,811
[45] Date of Patent: May 26, 1992

[54] TEMPERATURE MEASUREMENT AND COMPENSATION IN A FIBER-OPTIC SENSOR

[75] Inventors: Jerome T. Hartlaub, New Brighton; Jeffrey A. Schweitzer, St. Paul; George P. Seifert, Shoreview, all of Minn.

[73] Assignee: Medtronic, Inc., Minneapolis, Minn.

[21] Appl. No.: 516,621

[22] Filed: Apr. 30, 1990

[51] Int. Cl.⁵ ............................................... H61B 5/14
[52] U.S. Cl. .................................. 128/634; 128/633; 356/39
[58] Field of Search ............... 128/634, 636, 637, 736; 374/17-19, 141; 250/227.14, 227.18, 226; 356/412, 39-41

[56] References Cited

U.S. PATENT DOCUMENTS

| | | | |
|---|---|---|---|
| 4,200,110 | 4/1980 | Peterson et al. | |
| 4,362,645 | 12/1982 | Hof et al. | 374/160 |
| 4,476,870 | 10/1984 | Peterson et al. | 128/634 |
| 4,551,022 | 11/1985 | Tagaya | 250/226 |
| 4,560,286 | 12/1985 | Wickersheim | 128/736 |
| 4,710,623 | 12/1987 | Lipson et al. | 128/634 |
| 4,785,814 | 11/1988 | Kane | 128/634 |
| 4,842,783 | 6/1989 | Blaylock | 128/634 |
| 4,895,156 | 1/1990 | Schulze | 128/634 |

OTHER PUBLICATIONS

"Fiber-Optic Sensors for Biomedical Applications" by Peterson and Vurek, published in Science, Apr. 13, 1984, pp. 123 through 127.
"A New Non-Perturbing Temperature Probe Using Semiconductor Band Edge Shirt", published in Journal of Bioengineering, vol. 1, pp. 541 through 545, 1977.
"Thermometry and Dosimetry of Heat with Specific Reference to the Liquid-Crystal Optic Fiber Temperature Probe" by Livingston, published in Radiation and Environmental Biophysics, vol. 17, pp. 223 through 243, 1980.
"Optical-Fibre Thermometer for Medical Use" by Scheggi et al., published in IEE Proceedings, vol. 131, Pt.H, No. 4, Aug. 1984.

Primary Examiner—Stephen C. Pellegrino
Assistant Examiner—Steven J. Shumaker
Attorney, Agent, or Firm—Reed A. Duthler; Harold R. Patton

[57] ABSTRACT

A fiber-optic sensor for measuring a parameter of a test fluid, including a chemical sensor, incorporating a dye composition which displays changes in its optical properties correlated to changes in the parameter to be measured. The sensor is coupled to an apparatus including a light source, and means for measuring light received from said sensor at three different peak wavelengths. The first wavelength is chosen such that the optical characteristics of the dye with respect to that wavelength do not change significantly with changes in the parameter to be measured. The second and third wavelengths are chosen such that optical characteristics of the dye with respect to these wavelengths do change along with changes in the parameter to be measured, and also change as a function of temperature. The light received from the sensor at first, second and third wavelengths is compared to determine the temperature of the test fluid and to provide a temperature correction for the parameter to be measured.

7 Claims, 4 Drawing Sheets

TEMPERATURE MEASUREMENT AND COMPENSATION IN A FIBER-OPTIC SENSOR

BACKGROUND OF THE INVENTION

This invention relates generally to fiber-optic sensors and more particularly to fiber-optic colorimetric sensors.

Colorimetric fiber-optic sensors are known to the art. For example, pH and PCO2 sensors are described in the articles "Fiber-Optic pH Probe for Physiological Use", by Peterson et al, published in *Analytical Chemistry*, Vol. 52, pp. 864-869, 1980, and "A Fiber-Optic PCO2 Sensor", by Vorek et al, published in *Annals of Biomedical Engineering*, Vol. 11, pp. 499-510, 1983. Both sensors employ optical fibers to deliver light to and carry light from a sensor head which contains a phenol red based dye system. In both sensors, light absorption properties of phenol red are utilized in order to produce a color change which can be monitored optically. Fiber-optic sensors employing phenol red based dye systems are also disclosed in U.S. patent application Ser. No. 07/314,615, for "BLOOD GAS MONITORING SENSORS", by Schweitzer and Proctor, filed Feb. 23, 1989, now U.S. Pat. No. 5,047,208, and incorporated herein by reference in its entirety.

Phenol red is a weakly ionizing acid which disassociates into an acid form having an absorption peak at about 440 nm and a base form having an absorption peak at about 570 nm. The proportions of the acid and base forms are determined by the pH of the solution containing the dye. Therefore, the pH of the solution containing phenol red can be monitored using light from a green LED having a frequency band centered at or about 570 nm. Absorption at a second wavelength is also measured in order to compensate for changes in the overall performance of the sensor. Typically, the second wavelength employed is in the infrared range, at which the absorptive properties of phenol red are substantially the same whether in the acid or base form.

The light absorption properties of phenol red in the green wavelengths are also affected somewhat by temperature. Thus, the accuracy of pCO2 or pH measurements made using sensors according to the prior art if a separate temperature sensor is available. However, this complicates the measurement process and requires the use of additional equipment.

SUMMARY OF THE INVENTION

The absorptive characteristics of phenol red also vary substantially with pH and temperature in the vicinity of the absorbance peak for its acid form, at about 440 mm. It has been determined that the relative effects on absorption characteristics of phenol red due to changes in pH and due to changes in temperature also vary somewhat between the acid and base absorption peaks. The inventors have developed a method of measurement which takes advantage of this characteristic to allow the use of prior art pH and pCO2 sensors to measure temperature, and therefore to allow for temperature correction of pH and pCO2 measurements.

This is accomplished by coupling the fiber-optic sensor to an apparatus which includes light sources having three discrete wavelength peaks. In sensors employing phenol red based dyes, one wavelength peak is in the infrared range and the other two wavelength peaks are in the range in which absorption varies both with pH and temperature, for example 570 and 440 nm. Light reflected at 570 nm may be compared to light reflected at 830 nm and to light reflected at 440 nm and to calculate the temperature of the sensor and to produce a temperature corrected pH or PCO2 measurement. This is made possible because the proportional change in absorbance of the phenol red dye due to temperature change is greater in the vicinity of the absorbance peak for the acid form than in the vicinity of the absorbance peak for the base form.

The preferred embodiment of the present invention employs three individual light sources, each emitting light at a band centered at or near one of the desired three wavelengths. This is believed to be the most economical method of construction. However, the invention might also be practiced by employing a broad band light source, and dividing light received from the sensor into frequency bands centered on each of the three desired wavelengths.

DETAILED DESCRIPTION OF THE INVENTION

Figure 1:
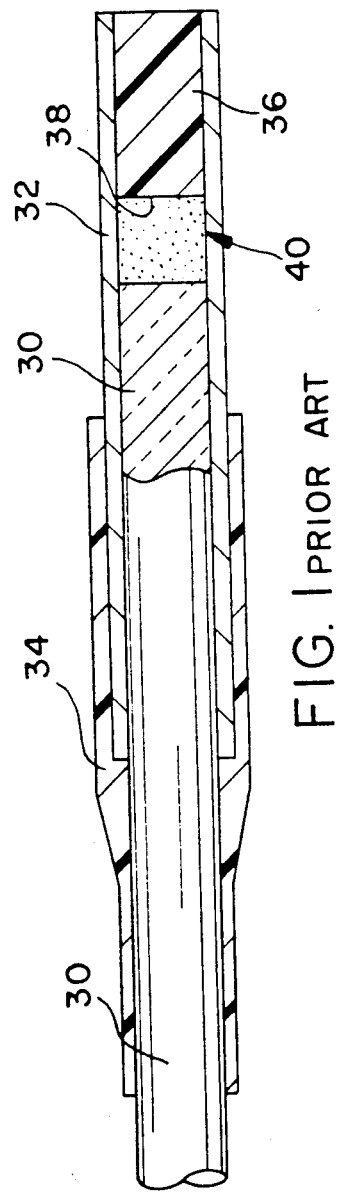
FIG. 1 shows a side, cutaway view through the distal end of a pH sensor of the type disclosed in the above cited Proctor and Schweitzer application.

FIG. 1 shows a side, cutaway view through a pH sensor of the type disclosed in the above-cited Proctor and Schweitzer application. The sensor assembly is mounted at the distal end of an optical fiber 30. Surrounding the optical fiber 30 is a semipermeable membrane 32, which may be a cellulosic membrane of the type typically used as dialysis tubing. Binding the membrane 32 to the optical fiber 30 is an adhesive 34, which may be a U-V curing epoxy. An epoxy plug 36 is located at the distal end of the sensor, and has been colored white by the addition of titanium dioxide. Its proximal surface 38 serves as a reflector for light emitted by the optical fiber 30 and the plug 36 itself serves to seal the distal end of the sensor by bonding to the cellulosic membrane 32. This construction provides an economical and readily reproduced sensor.

Dye chamber 40 is filled with a pH indicating dye, phenol red, bound to a polymeric substrate. One appropriate dye composition is discussed in more detail in U.S. patent application Ser. No. 07/314,561, for a "POLYMER DYE FOR FIBER-OPTIC SENSOR", filed on Feb. 23, 1989 by Fogt et al, now U.S. Pat. No. 4,906,249 assigned to the owner of the present application and incorporated by reference herein in its entirety.

In use, the sensor is inserted into blood, body fluid, or other liquid. Because the membrane 32 is permeable to hydrogen ions, the pH within the dye chamber will be the same as the pH of the liquid being measured. Changes in pH result in changes in the absorption characteristics of the phenol red dye, as discussed above.

Figure 2:
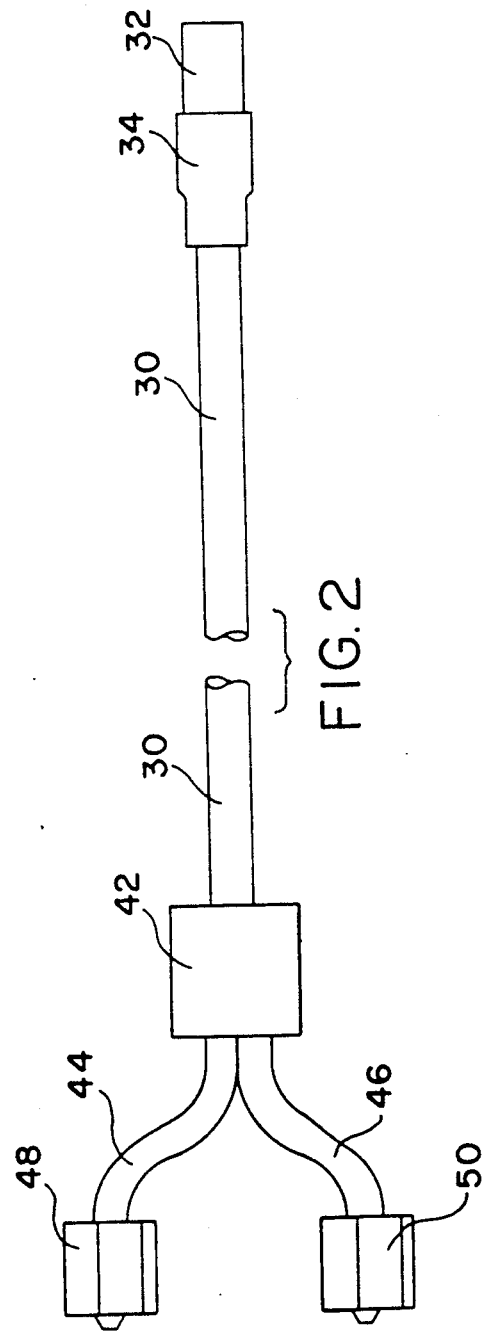
FIG. 2 shows a side, plan view of the sensor of FIG. 1.

FIG. 2 shows a side, plan view of the sensor of FIG. 1. Visible at the distal end of optical fiber 30 are the cellulosic membrane 32 which forms the outer skin of the sensor and the epoxy 34 which binds the cellulosic membrane to the optical fiber 30. At the proximal end of optical fiber 30 is an optical splitter/combiner 42 which allows the fiber 30 to be used both to transmit light to the sensor and collect light reflected from the sensor. Emerging from the proximal end of splitter/combiner 42 are first and second optical fiber paths 44 and 46, coupled to first and second optical couplers 48 and 50, respectively. Optical coupler 48 is intended to be coupled to sources of light at three discrete peak wavelengths, as discussed above. Optical coupler 50 intended to be coupled to a detector for measuring the amount of light reflected. In use, light at three separate wavelengths is sequentially applied to optical coupler 48, passes through optical fiber 44, combiner/splitter 42 and distally through optical fiber 30 to the dye 40 (FIG. 1) within the sensor. Light is reflected from the dye 40, propagates proximally through optical fiber 30, splitter/combiner 42 and optical fiber 46 to optical connector 50 which is coupled to a detector for measuring reflected light.

Figure 3:
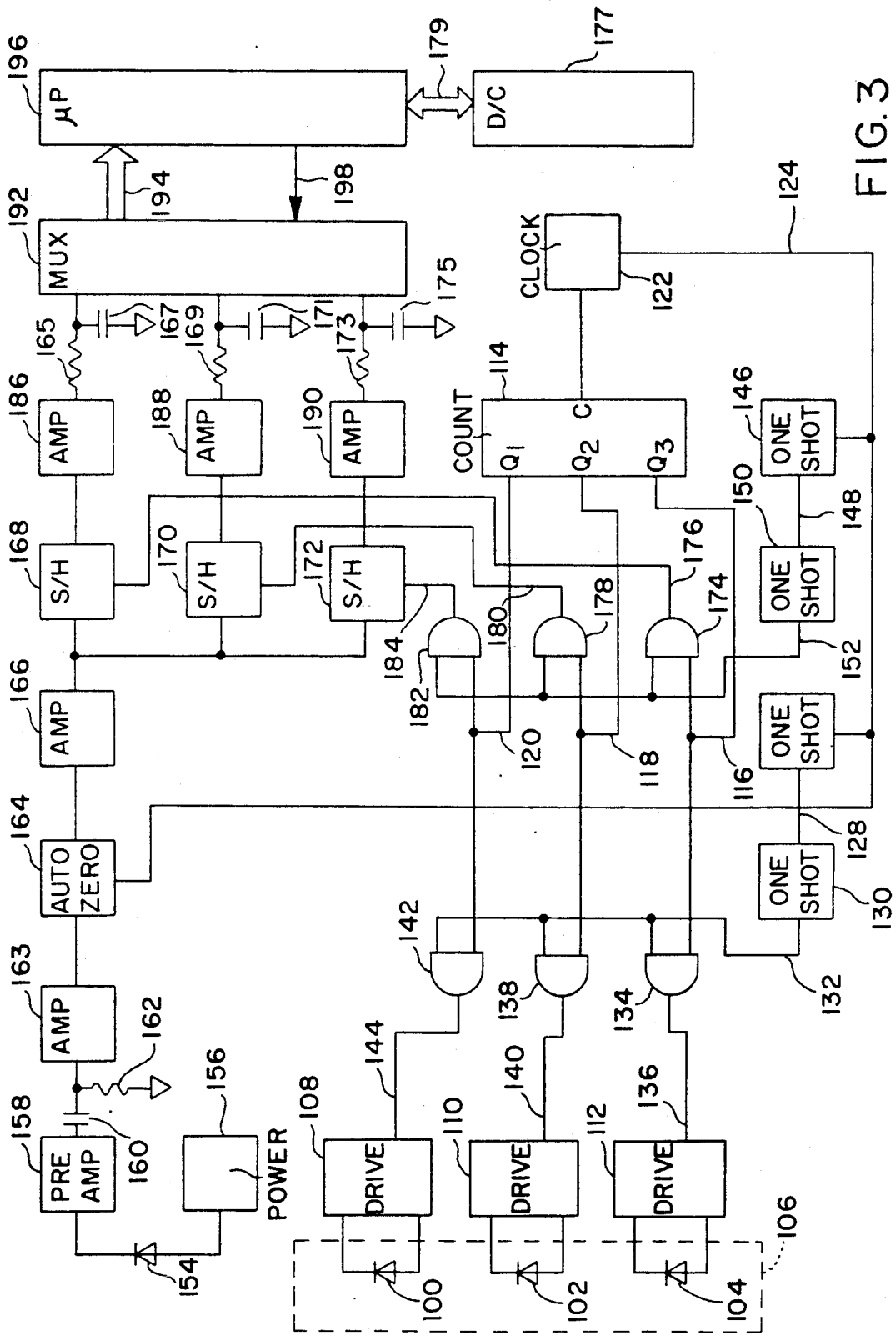
FIG. 3 shows a functional, block diagram of an apparatus appropriate for use with the sensor illustrated in FIGS. 1 and 2.

FIG. 3 is a block, functional diagram of an apparatus appropriate for use with the sensor of FIG. 1. The apparatus may also be used in conjunction with the $pCO_2$ sensor disclosed in the above-cited Proctor and Schweitzer application. The apparatus includes three light sources, 100, 102 and 104. Light source 100 has a frequency peak in the vicinity of the absorption peak for phenol red in its basic form. For example, LEDs are commercially available having wavelength peaks at or about 570 nm. Light source 102 has a wavelength peak near the absorption peak for the acid form of phenol red, but different from the wavelength of 440 nm is believed workable. Light source 104 has a frequency peak substantially in excess of 600 nm, in the frequency range in which absorption characteristics of the dye do not change significantly with variations in pH or temperature. For example, light source 104 may be an LED in the infrared range having a wavelength peak at about 830 nm. Light sources 100, 102 and 104 may take the form of three LED's mounted on a common substrate, providing all three wavelengths to a single optical fiber, as described in U.S. Pat. No. 4,725,128, issued Nov. 20, 1985, to Bornzin et al for a METHOD AND APPARATUS FOR DELIVERING LIGHT FROM MULTIPLE LIGHT EMITTING DIODES OVER A SINGLE OPTICAL FIBER, incorporated herein by reference in its entirety. Alternatively, light from light source 100, 102 and 104 may be applied to the ends of discrete optical fibers and combined using commerically available optical combiners. Light sources 100, 102 and 104 are powered by drivers 108, 110 and 112, respectively. Light sources 100, 102 and 104 are activated sequentially in individual measurement cycles, one measurement cycle for each light source.

Figure 4:
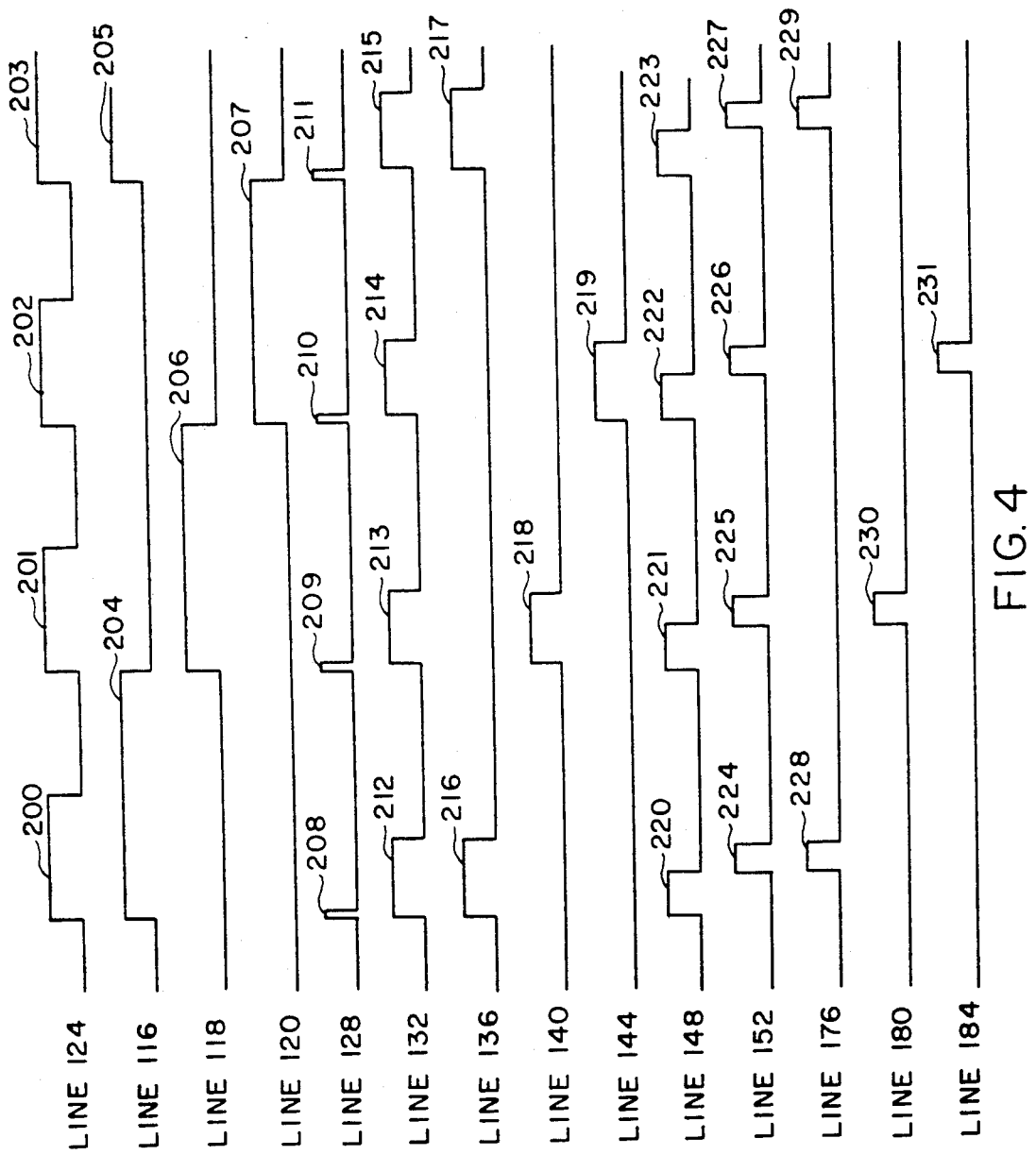
FIG. 4 is a timing diagram illustrating the function of the apparatus of FIG. 3.

Referring to FIG. 4, clock signals 200, 201, 202 and 203 are provided to ring counter 114, which sequentially generates 280 ms signals 204, 205, 206 and 207 on lines 116, 118 and 120, respectively. Signals 204 and 205 define measurement cycles associated with light source 104. Signal 206 defines a measurement cycle associated with light source 102. Signal 207 defines a measurement cycle associated with light source 100. Clock signals 200, 201, 202, 203 are also provided to one-shot 126 which in turn generates 10 ms trigger signals 208, 209, 210 and 211 on line 128. Trigger signals 208, 209, 210 and 211 cause one-shot 130 to generate 80 ms light source enabling signals 212, 213, 214, 215 on line 132. When signal 204 on line 116 and signal 212 on line 132 are simultaneously present, logic gate 134 generates an 80 ms signal 216 on line 136 which activates light source 104 via driver 112. Signal 205 on line 116 is generated in the same manner. When signal 206 on line 118 and signal 213 on line 132 are simultaneously present, logic gate 138 provides a signal 218 on line 140 which activates light source 102 via driver 110. Similarly, when signal 207 on line 120 and signal 214 on line 132 are simultaneously present, logic gate 142 generates a signal 219 on line 144 which activates light source 100 via driver 108. Thus, light sources 100, 102 and 104 are activated sequentially during successive measurement cycles. During each measurement cycle, the light reflected from the sensor is measured. This provides three values $R_B$ (reflectance at 440 nm), $R_G$ (reflectance at 570 nm) and $R_{IR}$ (reflectance at 830 nm). The measurements are used to calculate temperature and a temperature corrected value of the parameter the sensor is intended to measure.

Light reflected from the sensor is provided to an avalanche photodiode 154 which is powered by a negative 180 volt power supply 156. The output signal of photodiode 154 is amplified by preamp 158, filtered through a filter comprising capacitor 160 and resistor 162, and amplified again by amplifier 163. The amplified signal is passed through to the autozeroing circuit 164, and thence to buffer amplifier 166. The output of buffer amplifier is applied to the inputs of sample and hold circuits 168, 170 and 172, which are sequentially activated, one during each measurement cycle.

Referring again to FIG. 4, with each clock signal (200, 201, 202, 203) on line 124, one-shot 146 generates a 50 ms trigger pulse 220, 221, 222, 223 on line 148. Each of these trigger pulses is applied to one-shot 150 which in turn generates 30 ms sample and hold enable signals 224, 225, 226 and 227 on line 152. These sample and hold enable signals determine the times during which light reflected from the sensor is sampled and measured.

When sample and hold enable signal 224 on line 152 is present in conjunction with signal 204 on line 116, logic gate 174 provides a signal 228 on line 176 which activates sample and hold circuit 168. When sample and hold enable signal 225 is present on line 152 in conjunction with signal 206 on line 118, logic gate 178 provides a signal 230 on line 180 which activates sample and hold circuit 170. Similarly, when sample and hold enable signal 226 on line 152 is present concurrent with signal 207 on line 120, logic gate 182 generates a signal 231 on line 184 which activates sample and hold circuit 172.

The relative timing of the various periods set forth in FIG. 4 should be noted. One-shot 126 provides a delay in the initiation of the light source activation periods during each successive measurement cycle such that the light source activation period begins after the initiation of each measurement cycle by counter 114, and ends prior to the initiation of the next subsequent measurement cycle by counter 114. This allows the clock signal on line 124 to reset autozero circuit 164, assuring that the input to buffer amplifier 166 is zeroed between each measurement cycle. One-shot 146 delays the initiation of the sample and hold circuitry until after the activation of the LED used in that particular measurement cycle and ends sampling of reflected light prior to the turn off of the light source involved in that particular measurement cycle. This assures that the sample and hold circuitry will not be exposed to transients associated with turn on and turn off of the light sources.

The outputs of sample and hold circuits 168, 170 and 172 are provided to amplifiers 186, 188 and 190. These amplified signals are provided to A/D multiplexer 192 which sequentially converts the voltages present on the outputs of amplifiers 186, 188 and 190 to digital format on bus 194, providing it to microprocessor 196 for use in calculating temperature and corrected parameter measurements. Sequential selection of the outputs of amplifiers 186, 188 and 190 for conversion by A/D multiplexer 192 is accomplished via control line 198 from microprocessor 196. While microprocessor 196 may be any commercially available microprocessor, the inventors have found that an NEC brand multispeed lap top computer is satisfactory.

Microprocessor 196 may be used to calculate the temperature measurements and temperature corrected parameter measurements discussed above by use of a look-up table derived empirically by employing the probe to measure test solutions having known properties. The specific values entered in the look-up table will vary between different sensor designs.

Figure 5:
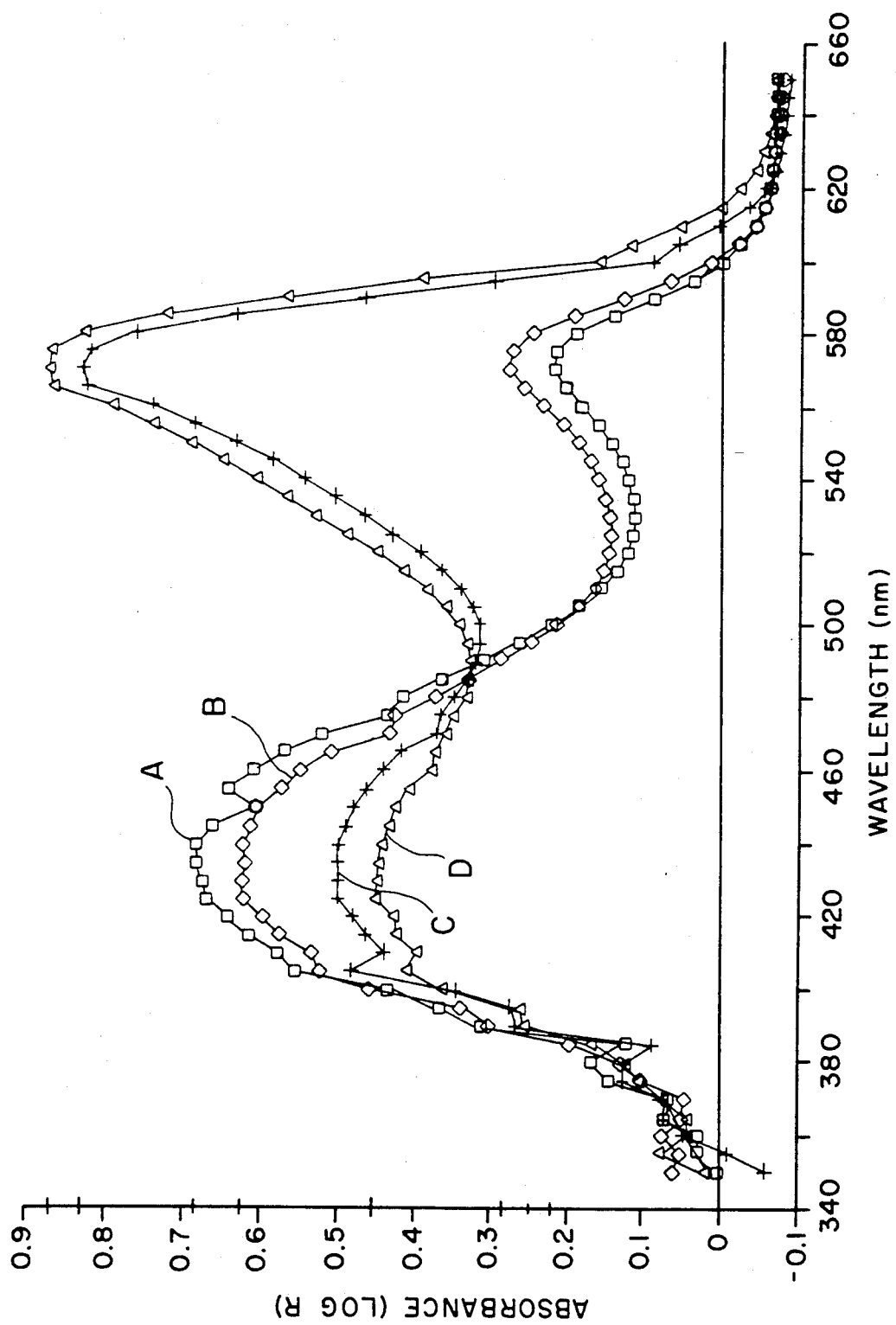
FIG. 5 is a chart illustrating the absorbance of a phenol red dye based on pH sensor at various pH's and temperatures.

FIG. 5 illustrates the absorbance of a phenol red based pH sensor as described above, measured in buffer solutions exhibiting pH changes of no more than 0.002/° C. Curve A illustrates the absorbance of the sensor in pH 6.88 buffer at 20° C. Curve B illustrates the absorbance of the sensor in a pH 6.84 buffer at 40° C. Curve C illustrates the absorbance of the sensor in a pH 7.82 buffer at 20° C. Curve D illustrates the absorbance of the sensor in a pH 7.78 buffer at 40° C. An examination of the curves shows a proportionally greater charge in absorbance at the acid peak 440 nm per degree centigrade than at the base peak 570 nm. Thus, measurement of the light reflected by the sensor at 830 nm, 570 nm and 440 nm will yield a three dimensional vector value ($R_B$, $R_G$, $R_{IR}$) which will uniquely identify the pH and temperature of the test solution when compared to stored pH and temperature values in the look-up table.

While the embodiment disclosed in the present specification is a sensor employing a phenol red based dye system, this invention is also believed applicable to other colorimetric sensors and sensors employing other dyes, especially those which display changes in absorbance with changes in pH. It is also believed other particular combinations of measurement wavelengths will be useful in sensors employing phenol red based dye systems and will be required in systems employing other dyes.

Similarly, while the embodiment disclosed in the present specification employs a system in which light is provided to the sensor by means of sequential activation of light sources having peaks at three differing frequencies, the invention might also alternatively be practiced in the context of a sensor activated by a broad spectrum light source, in which light from the sensor is divided spectrally into three frequency bands, and the amplitude of the reflected light at the three frequency bands is sequentially or simultaneously monitored. In this context, the invention might also be practiced using a dye which is fluorescent, in addition to or as an alternative to a dye which responds to changes in the measured parameter by changes in absorbance characteristics.

In conjunction with the above specification, we claim:

1. Apparatus for measuring a parameter of a test fluid comprising:
   a catheter including a sensor incorporating a dye which displays changes in light absorption properties correlated to changes in the parameter to be measured and in correlation to changes in temperature;
   means for applying first, second and third wavelengths of light to said sensor, said first wavelength chosen such that said absorptive characteristics of said sensor at said first wavelength do not change significantly with changes in said parameter to be measured, said second and third wavelengths chosen such that the absorptive characteristics of said sensor at both said second and third wavelengths do change in response to both changes in temperature and changes in said parameter to be measured; and
   means for measuring light reflected from said sensor at said first, second and third wavelengths to provide a temperature corrected measurement of said parameter to be measured.

2. Apparatus according to claim 1 wherein the dye within said sensor is phenol red, and wherein said first and third wavelengths are approximately 440 nm and 570 nm, respectively.

3. An apparatus according to claim 1 or claim 2 wherein said parameter to be measured comprises pH or carbon dioxide concentration.

4. A method of measuring a parameter of a test fluid by using a fiberoptic sensor containing a dye which displays changes in light absorption properties correlated to changes in the parameter to be measured, comprising:
   applying first, second and third wavelengths to said fiberoptic sensor while said sensor is in said test fluid, said first wavelength chosen such that absorptive characteristics of said dye at said first wavelength do not change significantly with changes in said parameter to be measured, said second and third wavelengths chosen such that the absorptive characteristics of said dye in said sensor at both said second and third wavelengths do change along with changes in both the parameter to be measured and with changes in temperature; and
   measuring light reflected from said sensor at said first, second and third wavelengths and comparing said measurements to provide a temperature corrected measurement of said parameter to be measured.

5. A method according to claim 4, wherein said dye comprises a phenol red dye, and wherein said first, second and third wavelengths are approximately 830 nm, 440 nm, and 570 nm, respectively.

6. An apparatus for measuring a parameter of a test fluid, comprising:
   a fiber-optic sensor including a dye which displays changes in optical properties correlated to changes in the parameter to be measured and in correlation to changes in temperature;
   means for applying light to said sensor;
   means for receiving light from said sensor, said means for applying and means for receiving together comprising means for measuring light received from said sensor at first, second and third wavelengths chosen such that said optical characteristics of said dye with respect to said first wavelength do not change significantly with changes in said parameter to be measured, said second and third wavelengths chosen such that said optical properties of said sensor at both said second and third wavelengths do change in both response to changes in temperature and changes in parameter to be measured; and means responsive to said measurement of said light received from said sensor to provide a temperature corrected measurement of said parameter.

7. A method of measuring a parameter of a test fluid by employing a fiber-optic sensor containing a dye which displays changes in optical properties correlated to changes in the parameter to be measured and correlated to temperatures, comprising:

applying light to said sensor while said sensor is in said test fluid;

measuring light reflected from said sensor, said measurement comprising measuring the relative amounts of light received from said sensor at first, second and third wavelengths, said first wavelength chosen such that said optical properties of said dye at said first wavelength do not change significantly with changes in said parameter to be measured, said second and third wavelength chosen such that said optical properties of said dye in said sensor at both said second and third wavelengths do change along with both changes in the parameter to be measured and with changes in temperature; and comparing said measurements to provide a temperature corrected measurement of said parameter.

* * * * *

UNITED STATES PATENT AND TRADEMARK OFFICE
CERTIFICATE OF CORRECTION

PATENT NO. : 5,115,811
DATED : May 26, 1992
INVENTOR(S) : Jerome T. Hartlaub, et. al.

It is certified that error appears in the above-indentified patent and that said Letters Patent is hereby corrected as shown below:

Column 6, line 25, before "and", insert --wave-length is approximately 830nm and wherein said second--.

Column 7, line 4, after "change in", delete --both--.

Column 7, line 5, after first occurrence of "changes in", insert --both--.

Signed and Sealed this

Twentieth Day of September, 1994

Attest:

BRUCE LEHMAN

Attesting Officer     Commissioner of Patents and Trademarks